United States Patent
Yi et al.

(10) Patent No.: US 9,442,212 B2
(45) Date of Patent: Sep. 13, 2016

(54) METHODS AND DEVICES FOR INSPECTING LIQUID

(71) Applicant: NUCTECH COMPANY LIMITED, Beijing (CN)

(72) Inventors: Yumin Yi, Beijing (CN); Li Zhang, Beijing (CN); Hongqiu Wang, Beijing (CN); Huacheng Feng, Beijing (CN); Jianhong Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 14/804,087

(22) Filed: Jul. 20, 2015

(65) Prior Publication Data
US 2016/0018557 A1  Jan. 21, 2016

(30) Foreign Application Priority Data

Jul. 21, 2014  (CN) .......................... 2014 1 0347354

(51) Int. Cl.
*G01J 3/44* (2006.01)
*G01N 11/00* (2006.01)
(Continued)

(52) U.S. Cl.
CPC ............. *G01V 5/0033* (2013.01); *G01N 21/65* (2013.01); *G01N 23/046* (2013.01); *G01N 23/087* (2013.01); *G01V 5/0008* (2013.01); *G01N 2021/651* (2013.01); *G01N 2201/0612* (2013.01)

(58) Field of Classification Search
CPC ...... G01N 5/00; G01N 21/255; G01N 21/65; G01N 21/3577; G01N 2201/06113; G01G 17/04; G01J 3/44
USPC .................. 356/301; 378/5; 73/53.01, 61.43; 702/25; 250/223 B, 338.1, 339.06; 382/142
See application file for complete search history.

(56) References Cited

U.S. PATENT DOCUMENTS 4,630,203 A * 12/1986 Szirtes ..................... A61B 6/00
                                                            356/2
5,642,393 A *  6/1997 Krug ..................... G01V 5/0016
                                                          376/159
(Continued)

FOREIGN PATENT DOCUMENTS

CN     101629916 A    1/2010
CN     102507532 A    6/2012
(Continued)

OTHER PUBLICATIONS

Masuda et al. Translation of JP 2007292704, Nov. 8, 2007.*
(Continued)

*Primary Examiner* — Tarifur Chowdhury
*Assistant Examiner* — Sunghee Y Gray
(74) *Attorney, Agent, or Firm* — Baker & Hostetler LLP

(57) ABSTRACT

Methods and devices for inspecting liquid are disclosed. According to the method, it is firstly determined whether the package of the liquid is transparent, semi-transparent, or opaque; in a case that the package of the liquid is transparent or semi-transparent, Raman spectrum analysis is implemented by a Raman spectrum module on the inspected liquid to judge whether the inspected liquid is dangerous or is suspected; and in a case that the package of the inspected liquid is opaque, the inspected liquid are inspected by using an X-ray dual-energy scanning technology to judge whether the inspected liquid is dangerous or is suspected. The above solution has advantages that the inspection speed is high, the material can be recognized, it is suitable for various packing materials with various shapes, the accuracy of the inspection result is high or the like. Therefore, the solution is suitable for security inspection in public places with high security inspection requirements, complicated inspected liquids, high personnel flow rate or the like.

17 Claims, 2 Drawing Sheets

(51) Int. Cl.
*G01N 33/00* (2006.01)
*G01N 31/00* (2006.01)
*G01N 21/90* (2006.01)
*G01J 5/00* (2006.01)
*G01J 5/02* (2006.01)
*G06K 9/00* (2006.01)
*G01V 5/00* (2006.01)
*G01N 21/65* (2006.01)
*G01N 23/04* (2006.01)
*G01N 23/087* (2006.01)

(56) References Cited

U.S. PATENT DOCUMENTS

| | | | |
|---|---|---|---|
| 7,840,360 B1 * | 11/2010 | Micheels | G01J 3/42 250/223 B |
| 2007/0017854 A1 | 1/2007 | Quine et al. | |
| 2008/0312768 A1 | 12/2008 | Ewing et al. | |
| 2009/0009753 A1 * | 1/2009 | Horai | G01N 21/65 356/237.3 |
| 2009/0092220 A1 * | 4/2009 | Chen | G01N 23/046 378/5 |

FOREIGN PATENT DOCUMENTS

| | | | |
|---|---|---|---|
| EP | 2196797 A1 | 6/2010 | |
| EP | 2685240 A1 | 1/2014 | |
| JP | 2007292704 | * 11/2007 | G01N 21/65 |

OTHER PUBLICATIONS

Ramirez et al.; Detection of Hazardous Liquids Concealed in Glass, Plastic and Aluminum Containers; Proceedings of SPIE; vol. 6538; Apr. 2007; 9 pages.

European Patent Application No. 15177776.0; Extended Search Report; dated Dec. 2, 2015; 11 pages.

Zhenggugan, Xu; "A Review of the development of the domestic and foreign liquid explosives security inspection equipment and technology"; Policy Technology; Nov. 2010; p. 51-53; (English Translation).

Industrial CT Technology and Principle; https://vpn.hw.sipo/proxy*86372237/n/print.ips; Jun. 2009; accessed Dec. 8, 2015; p. 74; (English Translation).

* cited by examiner

METHODS AND DEVICES FOR INSPECTING LIQUID

CROSS-REFERENCE TO RELATED APPLICATION

This application claims priority to the Chinese Patent Application No. 201410347354.3, filed on Jul. 21, 2014, entitled "METHODS AND DEVICES FOR INSPECTING LIQUID" which is incorporated herein by reference in its entirety.

TECHNICAL FIELD

The present disclosure relates to the field of radiation inspection technology and Raman spectrum analysis technology, and in particular, to a method and device for rapidly inspecting liquid and recognizing materials of the liquid by implementing X-ray dual-energy Computed Tomography (CT) scanning analysis and Raman spectrum analysis on the liquid.

BACKGROUND

In recent years, terrorists' means of violent terrorist activities in public places become increasingly diversified, and various dangerous liquids such as dangerous chemicals or the like also become one of the means of terrorist activities prejudicial to the public. Thereby, requirements for security inspection of liquid carried with persons are put forward on the basis of security inspection of luggage and parcels. As a result, there is a need for an effective method and device for security inspection, so as to meet the requirements.

Currently, there are four methods for inspecting liquid, which are a chemical method, an electromagnetic method, a neutron method and a ray method. These methods will be described in detail below.

The chemical method comprises odor recognition, ion scanning detection, and material analysis. The odor recognition often cannot be used for achieving inspection due to a sealed package of the liquids in practical applications. The ion scanning detection is famous for its high sensitivity. However, the ion scanning detection has the following disadvantages that it has a high false alarm rate and is often influenced by the background environment. The material analysis has features of high precise and high accuracy. However, the material analysis needs to take some time to analyze and process samples, which cannot meet the requirements for on-site rapid inspection. In addition, the material analysis may cause chemical pollution.

The electromagnetic method is an active measurement approach, and is used to distinguish liquids from each other according to different dielectric constants of the liquid relative to electromagnetic waves. However, the electromagnetic method per se is easy to be adversely influenced by metal packages, thick material packages, irregular special-shaped bottles or the like. Therefore, the electromagnetic method has obvious limitations in practical cases that the packing materials are complicated, and thus cannot be used for achieving material recognition.

A phenomenon of "neutron activation" may occur during the use of the neutron method. That is, radiation residuals may exist in the liquids after the liquids are inspected by using the neutron method. In addition, due to strong penetrability of neutrons, a more complicated radiation shield may be needed for neutrons, and devices may occupy a large area and be inconvenient to carry, and thus are not suitable for use in most public places.

The ray method comprises a two-dimensional ray scanning technology and a CT technology. In general, the two-dimensional ray scanning technology is primarily used for inspecting luggage articles and cannot be used for judging whether liquid is dangerous, and the CT technology has an advantage that it is not influenced by packing materials, and can be used for inspecting liquids. However, the CT technology has a relatively low inspection speed, and cannot be used for recognizing materials or the like.

In conclusion, the four methods described above have disadvantages in terms of rapid security inspection and material recognition of the liquid. Therefore, there is a need for a practical method to meet the requirements for rapid security inspection and material recognition of the liquid.

SUMMARY

In order to overcome the disadvantages existing in the related methods as described above, the purpose of the present disclosure is to provide a practical method and device for inspecting liquid and recognizing materials of the liquid by a combination of ray dual-energy CT scanning analysis and Raman spectrum analysis technologies. With the combination of these two technologies, the method and device can inspect the security of the liquid rapidly and accurately to obtain a result of whether the inspected liquid is secure, it can reduce the false alarm rate and missing report rate of the inspected liquid. At the same time, the Raman spectrum analysis technology can recognize the materials of the inspected liquid, which is beneficial for the security inspection department to implement qualitative analysis on the materials of the liquid which are checked to be dangerous and subsequent processing.

In an aspect of the present disclosure, a method for inspecting liquid is proposed. The method comprises steps of: determining whether the package of the liquid to be inspected is transparent, semi-transparent, or opaque; if the package of the liquid is transparent or semi-transparent, pointing a transparent or semi-transparent package portion of the inspected liquid at a laser output end of a Raman spectrum module and controlling the module to output a laser beam to implement Raman spectrum analysis on the inspected liquid, comparing the Raman spectrum of the inspected liquid with standard Raman spectrum of the liquid in a database to obtain an analysis result of the inspected liquid, and determining whether the inspected liquid is dangerous or suspicious; and if the package of the inspected liquid is opaque, inspecting it using an X-ray dual-energy scanning technology to obtain physical attribute information of the inspected liquid, comparing the obtained physical attribute information with standard predetermined information of the liquid in the database to obtain an analysis result of the inspected liquid, and determining whether the inspected liquid is dangerous or is suspected.

Preferably, when the difference between the physical attribute information which is obtained through inspection and the standard predetermined information is within a first predetermined threshold, it is judged that the inspected liquid is dangerous or is suspected.

Preferably, if the package of the liquid is opaque but has been opened, the method further comprising steps of: taking a part of the liquid out and putting it in a transparent package; pointing the transparent package with the laser output end of the Raman spectrum module, and controlling the module to output a laser beam to implement Raman spectrum analysis on the inspected liquid which has been taken out; and comparing the Raman spectrum of the inspected liquid with standard Raman spectrum of the liquid in the database to obtain an analysis result of the inspected liquid.

Preferably, when the difference between the Raman spectrum of the inspected liquid and the standard Raman spectrum is within a second predetermined threshold, it is judged that the inspected liquid is dangerous or is suspected, and the material of the inspected liquid is recognized at the same time.

In another aspect of the present disclosure, a device for inspecting liquid is proposed, the method comprises: an X-ray dual-energy scanning sub-system configured to inspect the liquid using an X-ray dual-energy scanning technology to obtain physical properties of the inspected liquid if the package of the inspected liquid is opaque; a Raman spectrum module configured to inspect the liquid to obtain corresponding Raman spectrum if the package of the liquid is made of a transparent or semi-transparent material; and a computer data processor connected to the ray dual-energy scanning sub-system and the Raman spectrum module and configured to compare the Raman spectrum of the inspected liquid with standard Raman spectrum of the liquid in a database to obtain an analysis result of the inspected liquid, and judge whether the inspected liquid is dangerous or is suspected, or compare the physical properties of the inspected liquid obtained by the X-ray dual-energy scanning sub-system with standard predetermined information of the liquid in the database to obtain an analysis result of the inspected liquid, and judge whether the inspected liquid is dangerous or is suspected.

Preferably, the Raman spectrum module comprises: a laser configured to emit a laser beam to illuminate the inspected liquid and to generate a Raman spectrum; a spectrometer configured to collect the signal and get Raman spectrum of the inspected liquid; and an external light path module connecting the laser and the spectrometer it is configured to enable the laser to illuminate the inspected liquid, and collect the Raman spectrum to the spectrometer.

Preferably, when the difference between the physical properties of the inspected liquid and the standard predetermined information is within the first predetermined threshold, it is judged that the inspected liquid is dangerous or is suspected.

Preferably, when the difference between the Raman spectrum of the inspected liquid and the standard Raman spectrum information is within a second predetermined threshold, it is judged that the inspected liquid is dangerous or is suspected, and materials of the inspected liquid is recognized at the same time.

Preferably, the external light path module is a fiber probe or a fiber-free probe.

Preferably, the Raman spectrum analysis module comprises one or more lasers, spectrometers and external light path modules.

Preferably, the ray dual-energy scanning sub-system comprises: a ray source configured to emit a ray; a detection and collection apparatus configured to detect and collect a ray signal which transmits through at least one inspected liquid; a controller configured to control the X-ray source and the detection and collection apparatus to implement dual-energy scanning on the inspected liquid to obtain projection data, reconstruct the projection data to obtain at least one physical property of the inspected liquid and at the same time control a bearer motion structure to implement Computed Tomography (CT) scanning motion on the inspected liquid and/or a linear motion structure to implement Digital Radiography (DR) scanning motion on the inspected liquid; the bearer motion structure configured to bearer at least one inspected liquid for ray dual-energy CT scanning motion; and the linear motion structure configured to bearer at least one inspected liquid for X-ray DR scanning motion.

Preferably, the ray dual-energy scanning sub-system can be configured to implement DR scanning on the inspected liquid to obtain a transmission image of the inspected liquid, judge whether the inspected liquid have an interlayer or hierarchical mixed liquids, and provide positions for the CT scanning.

Preferably, the physical properties obtained by the X-ray dual-energy scanning sub-system at least comprise a density and/or an atomic coefficient of the inspected liquid.

Preferably, the ray dual-energy scanning sub-system is configured to scan by using a high-energy ray and a low-energy ray and implement fusion analysis on the high-energy and low-energy scanned information.

Preferably, the computer data processor is configured to recognize materials of the inspected liquid using the Raman spectra obtained by the Raman spectrum module, and provide the name of the inspected liquid.

Preferably, the information obtained by Raman spectrum analysis at least comprises the Raman peak position and/or a Raman peak intensities of the inspected liquid.

Preferably, the computer data processor is a Personal Computer (PC) computer or an embedded processing unit.

Preferably, the computer data processor is configured to implement comparison using a predetermined recognition algorithm.

The device for security inspection according to the present disclosure has features that the X-ray dual-energy CT scanning analysis is not influenced by the packing material or the shape of the inspected liquid or the like and the Raman spectrum analysis has advantages that the inspection speed and accuracy is high, and, the material of the liquid can be recognized, it is suitable for various packing materials with various shapes, the accuracy of the inspection result is high or the like. Therefore, the device for security inspection is suitable for security inspection in public places with high security inspection requirements, complicated inspected liquid, high personnel flow rate or the like.

BRIEF DESCRIPTION OF THE DRAWINGS

For better understanding the present disclosure, the embodiments of the present disclosure will be described according to the following accompanying drawings.

Figure 1:
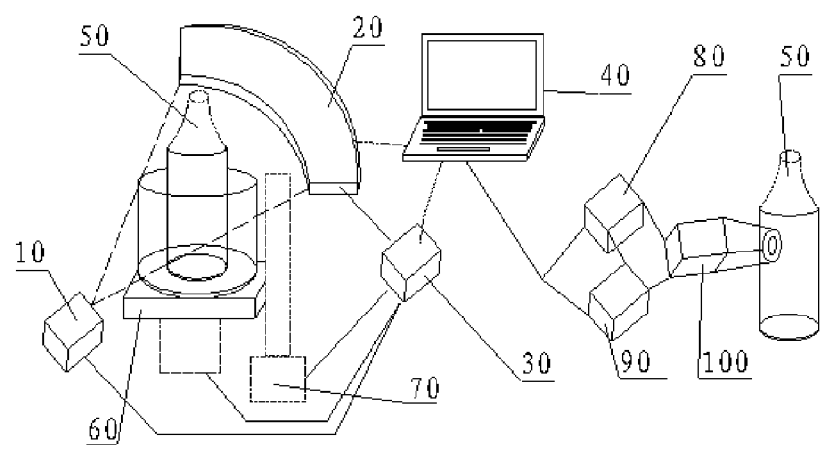
FIG. 1 is a structural diagram of an inspection device according to an embodiment of the present disclosure.

Not all circuits or structures in the embodiments are shown in the accompanying drawings. Throughout the accompanying drawings, the same reference signs represent the same or similar components or features.

DETAILED DESCRIPTION

Specific embodiments of the present invention will be described below in detail. It should be noted that the embodiments described herein are illustrated merely by way of example instead of limiting the present invention. In the following description, numerous specific details are set forth in order to provide a thorough understanding of the present invention. However, it is obvious to those skilled in the art that the present invention may be practiced without these specific details. In other instances, well known circuits, materials or methods have not been described in detail to avoid obscuring the present invention.

Reference throughout this specification to "one embodiment", "an embodiment", "one example" or "an example" means that a particular feature, structure, or characteristic described in connection with the embodiment or example is included in at least one embodiment of the present invention. Thus, the appearances of the phrase "in one embodiment", "in an embodiment", "one example" or "an example" in various places throughout this specification are not necessarily all referring to the same embodiment or example. Furthermore, the particular features, structures, or characteristics may be combined in any suitable combination and/or sub-combination in one or more embodiments or examples. In addition, those skilled in the art should understand that the accompanying drawings provided herein are illustrative, and are not necessarily drawn to scale. It should be understood that when an element is recited as being "coupled to" or "connected to" another element, the element can be directly coupled or coupled to the further element, or otherwise there may be an intervening element interposed therebetween. In contrary, when an element is recited as being "directly coupled to" or "directly connected to" another element, there is no intervening element interposed therebetween. The same reference numbers are used to refer to the same elements. A term "and/or" used herein comprises any or all combinations of one or more listed related items.

In order to overcome the disadvantages existing in the related methods as described above, some embodiments of the present disclosure provide a method and device for inspecting liquid, which can rapidly inspect the liquid by combining Raman spectrum analysis technology and X-ray dual-energy scanning analysis technology, to obtain a result of whether the inspected liquid is secure or dangerous.

In addition, the Raman spectrum analysis technology and the ray dual-energy scanning analysis technology may also be individually used for inspecting liquid, which is beneficial for the security inspection department to implement rapid inspection. For example, the Raman spectrum analysis technology may be individually used for inspecting liquid, and the ray dual-energy scanning technology may also be used for inspecting liquid.

In other embodiments of the present disclosure, a package of the inspected liquid is firstly observed, and if the package is made of transparent or semi-transparent material, the liquid is directly inspected using the Raman spectrum analysis technology. That is, a transparent or semi-transparent package portion of the inspected liquid is pointed at a laser output end of a Raman spectrum module and the laser output module is controlled to output a laser beam to implement Raman spectrum analysis on the inspected liquid, and the Raman spectrum of the inspected liquid is compared with standard Raman spectrum of the liquid in a database to obtain an analysis result of the inspected liquid. In addition, the material of the inspected liquid may be recognized.

If the package is made of opaque material, the inspected liquid is inspected using the X-ray dual-energy scanning technology to obtain physical properties of the inspected liquid, and the obtained physical properties are automatically compared with standard physical properties in the database, to obtain analysis result of the inspected liquid.

With respect to liquid in opaque package or liquid which has been opened and used but in which the name of the material cannot be determined, samples of the liquid may be taken out and put in a package made of transparent materials, and the samples are inspected and analyzed and the material of the samples is further recognized using the Raman spectrum analysis method to obtain an inspection result.

FIG. 1 is a structural diagram of an inspection device according to an embodiment of the present disclosure. As shown in FIG. 1, the inspection device according to the present embodiment comprises an X-ray dual-energy scanning sub-system and a Raman spectrum module. The X-ray dual-energy scanning sub-system comprises a ray source 10 configured to emit an X-ray; a detection and collection apparatus 20 configured to detect and collect an X-ray signal which transmits through at least one inspected liquid 50; a controller 30 configured to control the ray source and the detection and collection apparatus to implement dual-energy scanning on the inspected liquid 50 to obtain projection data, reconstruct the projection data to obtain at least one physical property (such as density, atomic coefficient or the like) of the inspected liquid 50 and at the same time control a bearer motion structure 60 to implement CT scanning motion on the inspected liquid and/or a linear motion structure 70 to implement Digital Radiography (DR) scanning motion on the inspected liquid; the bearer motion structure 60 configured to bearer at least one inspected liquid 50 for X-ray dual-energy CT scanning motion; and the linear motion structure 70 configured to bearer at least one inspected liquid 50 for X-ray DR scanning motion.

As shown, the Raman spectrum module comprises a laser 80 configured to emit a laser beam to illuminate the inspected liquid and generate a Raman spectrum; a spectrometer 90 configured to collect the signal and get the Raman spectrum of the liquid; an external light path module 100 configured to enable the laser to illuminate the inspected liquid 50, and collect the Raman spectrum of the inspected liquid 50 to the spectrometer 90; and a computer data processor 40 configured to process the data analysis, and output an inspection result.

In some embodiments, the external light path module 100 is a fiber probe or a fiber-free probe. In some embodiments, the Raman spectrum analysis module may comprise one or more lasers, spectrometers and external light path modules. The Raman spectrum module is used to rapidly inspect the liquid in cooperation with the computer data processor.

As shown in FIG. 1, the computer data processor 40 may be a Personal Computer (PC) computer or an embedded processing unit. In addition, the computer data processor may implement comparison by using a predetermined recognition algorithm.

Figure 2:
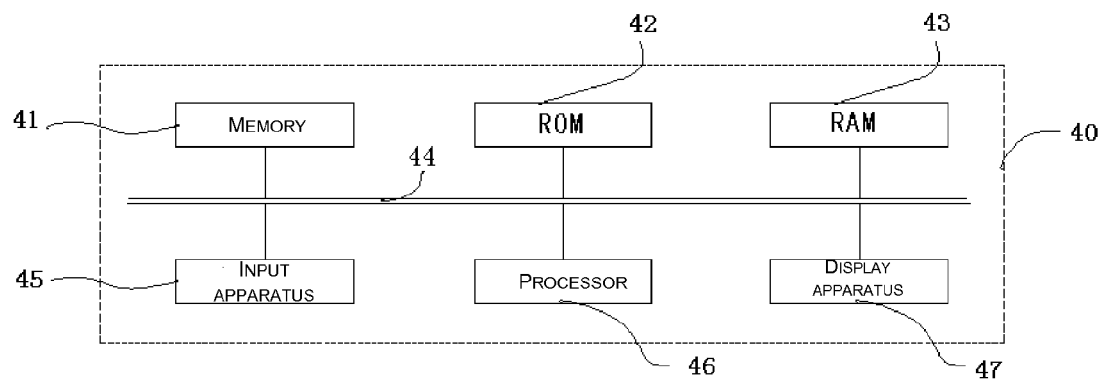
FIG. 2 illustrates a structural diagram of a data processor in the inspection device illustrated in FIG. 1.

FIG. 2 illustrates a structural block diagram of the computer data processor 40 illustrated in FIG. 1. As shown in FIG. 2, data collected by the data collector is stored in a memory 41. A Read Only Memory (ROM) 42 stores configuration information and programs of the computer data processor. A Random Access Memory (RAM) 43 is used to temporally store various data during the operation of the processor 46. In addition, the memory 41 also stores computer programs for data processing. An internal bus 44 is used to connect the memory 41, the ROM 42 and the RAM 43 described above and an input apparatus 45, a processor 46 and a display apparatus 47.

After a user inputs an operation command through the input apparatus 45 such as a button, a sensor, a keyboard, a mouse or the like, the instruction codes in the computer programs instruct the processor to implement a predetermined data processing algorithm, and after a data processing result is obtained, the data processing result is displayed on the display apparatus 47 such as a Liquid Crystal Display (LCD) display or the like, or the processing result is directly output in a form of hard copy.

Figure 3:
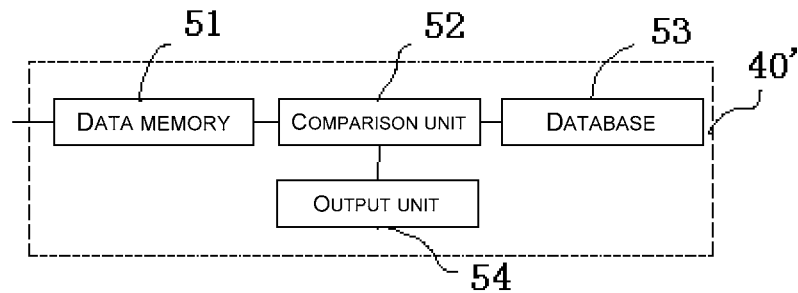
FIG. 3 illustrates a functional diagram of a computer processor in the inspection device illustrated in FIG. 1.

FIG. 3 illustrates a functional block diagram of a computer data processor 40' in the inspection device illustrated in FIG. 1. As another example of computer data processing, the computer data processor 40' comprises a data memory 51 which may store information related to programs, database or the like; a comparison unit 52 configured to compare the Raman spectrum of the inspected liquid 50 with the standard Raman spectrum of the liquid in the database, to determine recognition information of the inspected liquid 50; a database 53 primarily configured to store the predetermined standard Raman spectra; and an output unit 54 for example a display or another output device, configured to directly present the recognition information obtained by the comparison unit 52 to an operator.

In some embodiments, when the difference between the physical properties which is obtained by using the X-ray dual-energy scanning technology and the standard predetermined information is within a first predetermined threshold, for example, 1%, it is judged that the inspected liquid is suspected.

Preferably, when the difference (a peak difference or a peak position difference) between the Raman spectrum of the inspected liquid and the standard Raman spectrum is within a second predetermined threshold, it is judged that the inspected liquid is suspected.

According to an embodiment of the present disclosure, the X-ray dual-energy CT scanning analysis may be used to implement DR scanning on the inspected liquid to obtain a transmission image of the inspected liquid and to implement CT scanning on the inspected liquid to obtain physical properties of the inspected liquid.

According to an embodiment of the present disclosure, the X-ray dual-energy CT scanning analysis may be used to implement DR scanning on the inspected liquid to obtain a transmission image of the inspected liquid, judge whether the inspected liquid have an interlayer, hierarchical mixed liquids or the like, and provide a basis of positioning for the CT scanning.

According to an embodiment of the present disclosure, the function of implementing, by using the X-ray dual-energy CT scanning analysis, DR scanning on the inspected liquid is not necessary. According to the requirements for security inspection, the DR scanning may not be implemented on the inspected liquid.

According to an embodiment of the present disclosure, the physical properties obtained by using the X-ray dual-energy CT scanning analysis at least comprises a density and/or an atomic coefficient of the inspected liquid.

According to an embodiment of the present disclosure, in the X-ray dual-energy CT scanning analysis, the dual energy comprises a high-energy X-ray and a low-energy X-ray, and the X-ray dual-energy CT scanning analysis comprises fusion analysis on the high-energy and low-energy scanned information.

According to an embodiment of the present disclosure, the Raman spectrum analysis technology can be used to recognize the materials of the inspected liquid, which is beneficial for the security inspection department to implement qualitative analysis on the materials of the liquid which are judged to be dangerous and subsequent processing.

According to an embodiment of the present disclosure, the Raman spectrum analysis module may comprise one or more lasers, spectrometers and external light path modules (for example fiber probes or fiber-free probes).

According to an embodiment of the present disclosure, the information obtained using the Raman spectrum analysis at least comprises Raman peak positions and/or Raman peak intensities of the inspected liquid. According to an embodiment of the present disclosure, the computer data processor may be a PC computer or an embedded processing unit. According to an embodiment of the present disclosure, the computer data processor may be configured to implement comparison by using a predetermined recognition algorithm. According to an embodiment of the present disclosure, although the device for inspecting liquid using the combination of X-ray dual-energy CT scanning analysis and Raman spectrum analysis technologies has been disclosed, the method and device may use the combination of the X-ray dual-energy CT scanning analysis and Raman spectrum analysis technologies or may also individually use the X-ray dual-energy CT scanning analysis technology or the Raman spectrum analysis technology.

Figure 4:
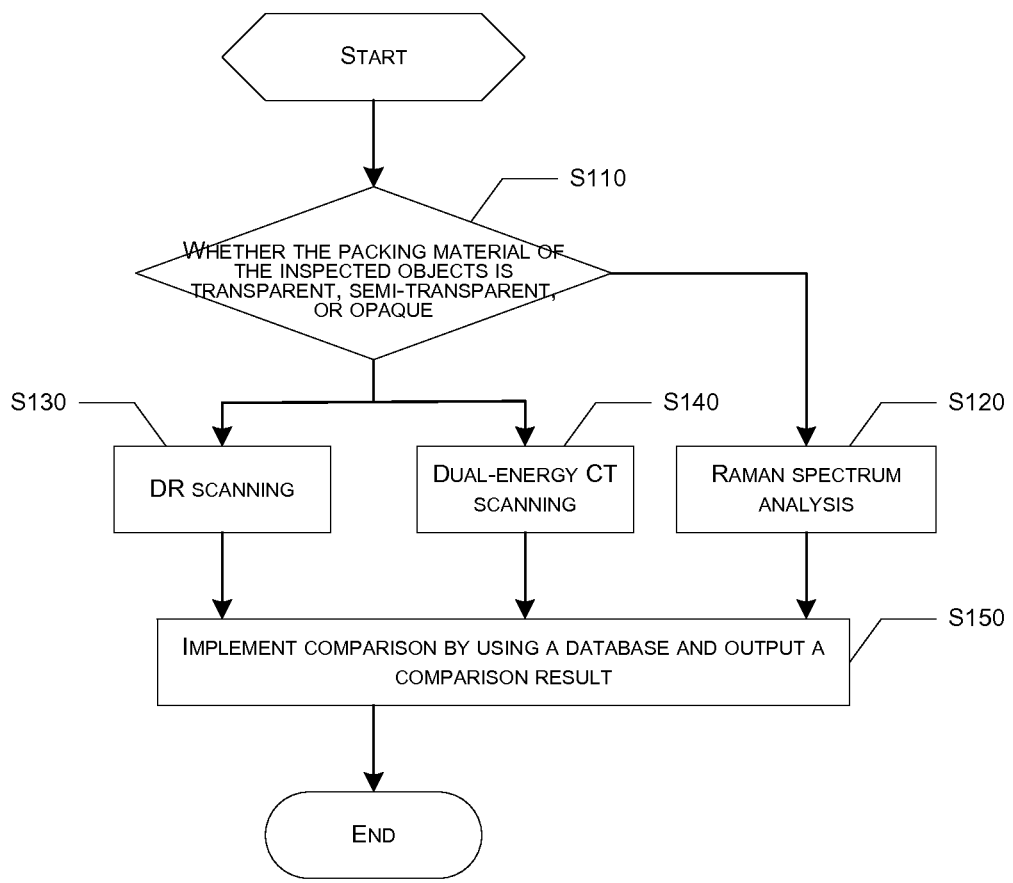
FIG. 4 is a flowchart of an inspection method according to an embodiment of the present disclosure.

FIG. 4 illustrates a flowchart of an inspection method according to an embodiment of the present disclosure.

As shown in FIG. 4, in step S110, a packing material of inspected liquid 50 is observed and judged to select different inspection methods according to different packing materials. In step S120, if the packing material is transparent or semi-transparent, the inspected liquid 50 is placed at an external light path module 100 of a Raman spectrometer to be directly inspected, and the inspection information is transmitted to a computer data processor 40.

In steps S130 and S140, if the packing material is opaque, the inspected liquid 50 are placed on a bearer motion structure 60, a linear motion structure 70 is controlled to implement DR scanning on the inspected liquid 50, and then the bearer motion structure 60 is controlled to implement CT scanning on the inspected liquid 50 to obtain X-ray dual-energy CT scanning information, which is transmitted to the computer data processor 40.

In step S150, the computer data processor 40 automatically compares the received data with the standard data or predetermined data in the database 50, and a comparison result is automatically displayed on an output unit 54.

Although the embodiments described above are described by means of combining the Raman spectrum technology and the X-ray dual-energy scanning technology, in other embodiments, the Raman spectrum inspection or X-ray dual-energy scanning may also be directly implemented on the inspected liquid for comparison, regardless of whether the package is transparent or semi-transparent.

In addition, in a case that the package of the liquid can be opened or has been opened, a part of the liquids are taken out to be inspected by using the Raman spectrum technology. For example, a part of the liquid may be taken out from the liquid and put in a transparent package, then the transparent package is pointed to a laser output end of the Raman spectrum module and the module is controlled to emit a laser beam to implement Raman spectrum analysis on the inspected liquid. The Raman spectrum of the inspected liquid is compared with the standard Raman spectrum of the liquid in the database, to obtain an analysis result of the inspected liquid.

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. A method for inspecting liquid, comprising steps of:
   determining whether the package of liquid is transparent, semi-transparent, or opaque;
   if the package of the liquid is transparent or semi-transparent, pointing a transparent or semi-transparent package portion of the inspected liquid to a laser output end of a Raman spectrum module and controlling the module to output a laser beam to implement Raman spectrum analysis on the inspected liquid, comparing the Raman spectrum of the inspected liquid with standard Raman spectrum of the liquid in a database to obtain an analysis result of the inspected liquid, and judging whether the inspected liquid is dangerous or is suspected; and
   if the package of the inspected liquid is opaque, inspecting the inspected liquid using an X-ray dual-energy scanning technology to obtain physical properties of the inspected liquid, comparing the obtained physical properties with standard predetermined information of the liquid in the database to obtain an analysis result of the inspected liquid, and judging whether the inspected liquid is dangerous or is suspected.

2. The method according to claim 1, wherein when the difference between the physical properties which is obtained through inspection and the standard predetermined information is within a first predetermined threshold, it is judged that the inspected liquid is dangerous or is suspected.

3. The method according to claim 1, wherein in a case that the package of the liquid is opaque but has been opened, the method further comprising steps of:
   taking a part of liquid out from the liquid and putting it in a transparent package;
   pointing the transparent package to the laser output end of the Raman spectrum module, and controlling the module to output a laser to implement Raman spectrum analysis on the inspected liquid which has been taken out; and
   comparing the Raman spectrum of the inspected liquid with standard Raman spectrum of the liquid in the database to obtain an analysis result of the inspected liquid.

4. The method according to claim 3, wherein when the difference between the Raman spectrum of the inspected liquid and the standard Raman spectrum is within a second predetermined threshold, it is judged that the inspected liquid is dangerous or is suspected, and materials of the inspected liquid is recognized at the same time.

5. A device for inspecting liquid, comprising:
   an X-ray dual-energy scanning sub-system configured to inspect the liquid using an X-ray dual-energy scanning technology to obtain physical properties of the inspected liquid if a package of the inspected liquid is opaque;
   a Raman spectrum module configured to inspect the inspected liquid to obtain corresponding Raman spectrum if the package of the liquid is made of a transparent or semi-transparent material, wherein a transparent or semi-transparent package portion of the inspected liquid is pointed to a laser output end of the Raman spectrum module and the Raman spectrum module is further configured to output a laser beam to implement Raman spectrum analysis on the inspected liquid; and
   a computer data processor connected to the X-ray dual-energy scanning sub-system and the Raman spectrum module, configured to compare the Raman spectrum of the inspected liquid with standard Raman spectrum of the liquid in a database to obtain an analysis result of the inspected liquid and judge whether the inspected liquid is dangerous or is suspected, and configured to compare the physical properties of the inspected liquid obtained by the X-ray dual-energy scanning sub-system with standard predetermined information of the liquid in the database to obtain an analysis result of the inspected liquid and judge whether the inspected liquid is dangerous or is suspected.

6. The device according to claim 5, wherein the Raman spectrum module comprises:
   a laser configured to emit a laser beam to illuminate the inspected liquid and generate a Raman spectrum;
   a spectrometer configured to collect the Raman signal of the inspected liquid; and
   an external light path module connected the laser and the spectrometer and configured to, enable the laser illuminate the inspected liquid, and transmit the Raman signal to the spectrometer.

7. The device according to claim 5, wherein when the difference between the physical properties obtained through inspection and the standard predetermined information is within a first predetermined threshold, it is judged that the inspected liquid is dangerous or is suspected.

8. The device according to claim 5, wherein when the difference between the Raman spectrum of the inspected liquid and the standard Raman spectrum information is within a second predetermined threshold, it is judged that the inspected liquid is dangerous or is suspected, and materials of the inspected liquid is recognized at the same time.

9. The device according to claim 6, wherein the external light path module is a fiber probe or a fiber-free probe.

10. The device according to claim 5, wherein the X-ray dual-energy scanning sub-system comprises:
    a ray source configured to emit an X-ray;
    a detection and collection apparatus configured to detect and collect an X-ray signal which transmits through at least one inspected liquid;
    a controller configured to control the X-ray source and the detection and collection apparatus to implement X-ray dual-energy scanning on the inspected liquid to obtain projection data and reconstruct the projection data to obtain at least one physical attribute information of the inspected liquid;
    a first motion structure configured to bear at least one inspected liquid for X-ray dual-energy CT scanning motion; and
    a second motion structure configured to bear at least one inspected liquid for ray DR scanning motion,
    wherein the controller is further configured to control the first motion structure to implement Computed Tomography (CT) scanning motion on the inspected liquid and the second motion structure to implement Digital Radiography (DR) scanning motion on the inspected liquid.

11. The device according to claim 10, wherein the X-ray dual-energy scanning sub-system can be configured to implement DR scanning on the inspected liquid to obtain a transmission image of the inspected liquid, judge whether the inspected liquid have an interlayer or hierarchical mixed liquid, and provide positions for the CT scanning.

12. The device according to claim 5, wherein the physical properties obtained by the X-ray dual-energy scanning sub-system at least comprises a density and/or an atomic coefficient of the inspected liquid.

13. The device according to claim 5, wherein the X-ray dual-energy scanning sub-system is configured to scan using a high-energy X-ray and a low-energy X-ray and implement fusion analysis on the high-energy and low-energy scanned information.

14. The device according to claim 5, wherein the computer data processor is configured to recognize materials of the inspected liquid by using the Raman spectrum obtained by the Raman spectrum module, and provide the name of the inspected liquid.

15. The device according to claim 5, wherein the information obtained by using Raman spectrum analysis at least comprises a Raman peak position and/or Raman peak intensities of the inspected liquid.

16. The device according to claim 5, wherein the computer data processor is a Personal Computer (PC) computer or an embedded processing unit.

17. The device according to claim 5, wherein the computer data processor is configured to implement comparison using a predetermined recognition algorithm.

* * * * *